(12) United States Patent
Rangarajan et al.

(10) Patent No.: US 6,774,989 B1
(45) Date of Patent: Aug. 10, 2004

(54) INTERLAYER DIELECTRIC VOID DETECTION

(75) Inventors: Bharath Rangarajan, Santa Clara, CA (US); Michael K. Templeton, Atherton, CA (US); Arvind Halliyal, Sunnyvale, CA (US); Bhanwar Singh, Morgan Hill, CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 0 days.

(21) Appl. No.: 10/050,453

(22) Filed: Jan. 16, 2002

(51) Int. Cl.[7] .............................................. G01N 21/00
(52) U.S. Cl. ................... 356/237.2; 356/237.4
(58) Field of Search .................. 356/237.1–237.5; 250/559.01, 559.04, 559.05, 559.06

(56) References Cited

U.S. PATENT DOCUMENTS

| | | | | |
|---|---|---|---|---|
| 4,330,213 A | | 5/1982 | Kleinknecht et al. ........ 356/355 |
| 4,978,862 A | * | 12/1990 | Silva et al. ............ 250/559.45 |
| 5,042,952 A | * | 8/1991 | Opsal et al. ................. 356/432 |
| 5,138,176 A | | 8/1992 | Nishi .......................... 250/548 |
| 5,164,790 A | | 11/1992 | McNeil et al. .............. 356/355 |
| 5,208,648 A | * | 5/1993 | Batchelder et al. ....... 356/237.1 |
| 5,293,538 A | * | 3/1994 | Iwata et al. .............. 356/239.1 |
| 5,301,012 A | * | 4/1994 | King et al. .................. 356/398 |
| 5,708,279 A | * | 1/1998 | Cheng ................... 250/559.22 |
| 5,835,226 A | * | 11/1998 | Berman et al. ............. 356/632 |
| 5,903,343 A | * | 5/1999 | Ning et al. ............... 356/341.1 |
| 5,982,482 A | * | 11/1999 | Nelson et al. ........... 356/237.1 |
| 6,023,327 A | * | 2/2000 | Shabde et al. ........... 356/237.1 |
| 6,266,137 B1 | * | 7/2001 | Morinaga ................. 356/237.1 |
| 6,327,035 B1 | * | 12/2001 | Li et al. ...................... 356/432 |
| 6,451,700 B1 | * | 9/2002 | Stirton et al. ............... 438/695 |
| 6,545,753 B2 | * | 4/2003 | Subramanian et al. ... 356/237.5 |

* cited by examiner

*Primary Examiner*—Michael P. Stafira
(74) *Attorney, Agent, or Firm*—Amin & Turocy, LLP

(57) ABSTRACT

A system for detecting voids in an ILD layer is provided. The system includes one or more light sources, each light source directing light to respective portions of the ILD layer. Light reflected from the respective portions is collected by a measuring system that processes the collected light. The collected light is indicative of the presence of voids in the respective portions of the ILD layer. The measuring system provides ILD layer void related data to a processor that determines whether voids exist in the respective portions of the ILD layer. The processor selectively marks the ILD layer portions to facilitate further processing and/or destruction of the IC with the ILD layer voids.

11 Claims, 16 Drawing Sheets

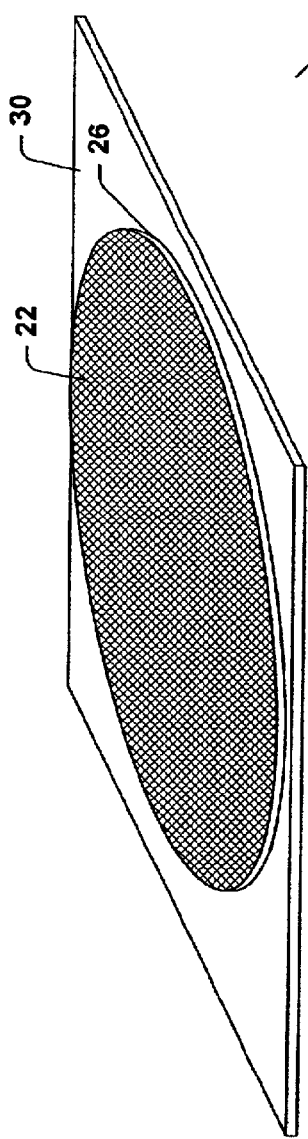
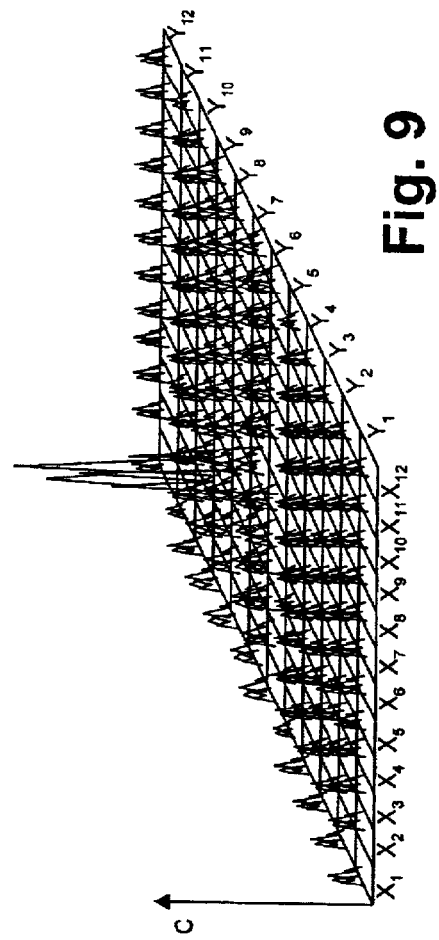
Fig. 8
Fig. 9
Fig. 10

US 6,774,989 B1

INTERLAYER DIELECTRIC VOID DETECTION

Technical Field

The present invention generally relates to semiconductor processing, and in particular to a system for monitoring inter layer dielectric deposition.

BACKGROUND

In the semiconductor industry, there is a continuing trend toward higher device densities. To achieve these higher densities, efforts continue toward scaling down device dimensions (e.g., at sub-micron levels) on semiconductor wafers. To accomplish such high device packing densities, smaller and smaller feature sizes are required. This may include the width and spacing of interconnecting lines, spacing and diameter of contact holes, and the surface geometry such as corners and edges of various features. Similarly, finer and more uniform layers of inter layer dielectrics (hereinafter ILDs) are required to separate such features. For reasons that will be described below, void formation in the ILDs should be mitigated and/or prevented.

The process of manufacturing semiconductors, or integrated circuits (commonly called ICs, or chips) typically consists of more than a hundred steps, during which hundreds of copies of an integrated circuit may be formed on a single wafer. Generally, the process involves creating several patterned layers on and into the substrate that ultimately forms the complete integrated circuit This layering process creates electrically active regions in and on the semiconductor wafer surface. To isolate the active regions or layers, ILDs are typically formed over them.

In most conventional IMD deposition processes, chemical vapor deposition is performed, where a solid film of oxide is formed on a substrate by the reaction of an oxide gas and the substrate. Various parameters such as the oxide source and deposition method influence the characteristics of the resulting ILD. In chemical vapor deposition, gas mixture, temperature, RF power, pressure and gas flow rare, among other factors, may be varied to achieve the desired characteristics.

Undesired fluctuations in any one or a combination of these parameters may lead to void formation in the ILD. In many current applications, ILD formation must conform to exacting specifications in order to mitigate or prevent void formation. A void present in the ILD may cause electrical shorting (short circuits), cracking in the circuit, and/or lead to an open circuit depending on the size and location of the void. For example, voids which exceed about 25% of a structure width and/or are higher than the structure surface in height tend to cause any one or a combination of these problems. Voids which are formed early on in the semiconductor fabrication process but are undetected until further processing has been done may exacerbate or cause even more problems, resulting in an inoperable device.

With the requirement of smaller and smaller features and higher device densities, detection and mitigation of void formation is even more critical to the fabrication of operable and effective semiconductor devices. Thus, to detect the formation of voids, including their size and number, an efficient system/method to monitor ILD deposition for void formation and detection is desired to increase the reliability and performance of semiconductor devices.

SUMMARY

The following presents a simplified summary of the invention in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

The present invention provides for a system that facilitates controlling inter layer dielectric (hereinafter "ILD") deposition and detecting void formation in the ILD via scatterometry. Scatterometry is a technique that involves directing a light beam, typically a laser, on an area to be characterized and measuring the angular distribution of the light that is elastically scattered from that area An exemplary system may employ one or more light sources arranged to project light on respective portions of an ILD layer and one or more light detecting devices to collect light reflected by the ILD and/or light passing through the ILD. The light reflected from the ILD is indicative of the presence of voids in the ILD. The presence of ILD voids is monitored and detected by the system, and semiconductor devices with ILD voids may be marked for further processing and/or discarded. As a result, fewer semiconductors and integrated circuit chips with ILD voids are produced.

One particular aspect of the invention relates to a system for detecting and monitoring ILD void formation. A system for directing light directs light to a portion of the ILD, and a measuring system measures parameters of the ILD based on light reflected from the ILD. A processor is operatively coupled to the measuring system, and receives ILD parameter data from the measuring system. By comparing the collected parameter data with a database comprised of known ILD layers, each having at least one void present, the processor uses the collected data to detect and monitor void formation in the ILD.

Yet another aspect of the present invention relates to a method for detecting and monitoring ILD void formation. The method comprises defining an ILD layer as a plurality of portions and then directing light onto at least one of the portions. Light reflected from the at least one portion is collected and analyzed to determine whether there are voids in the at least one portion. If void formation is detected in the at least one portion, such void formation may be monitored to determine the extent and dimensions of the void and/or selectively marked to be discarded.

Still another aspect of the present invention relates to a system for detecting and monitoring ILD void formation including a means for directing light onto a plurality of portions of an ILD layer, a means for collecting light from the respective ILD layer portions and a means for analyzing the collected light to determine whether there is void formation in the respective ILD layer portions.

To the accomplishment of the foregoing and related ends, the invention, then, comprises the features hereinafter fully described and particularly pointed out in the claims. The following description and the annexed drawings set forth in detail certain illustrative embodiments of the invention. But these embodiments are indicative of only a few of the various ways in which the principles of the invention may be employed. Other objects, advantages and novel features of the invention will become apparent from the following detailed description of the invention when considered in conjunction with the drawings.

BRIEF DESCRIPTION OF THE DRAWINGS

FIG. 8 is a perspective illustration of a substrate having an ILD layer formed thereon in accordance with the present invention.

FIG. 9 is a representative three-dimensional grid map of an ILD layer illustrating void measurements taken at grid blocks of the grid map in accordance with the present invention.

FIG. 10 is a void measurement table correlating the void measurements of FIG. 4 with desired values for the void measurements in accordance with the present invention.

DETAILED DESCRIPTION

Figure 1:
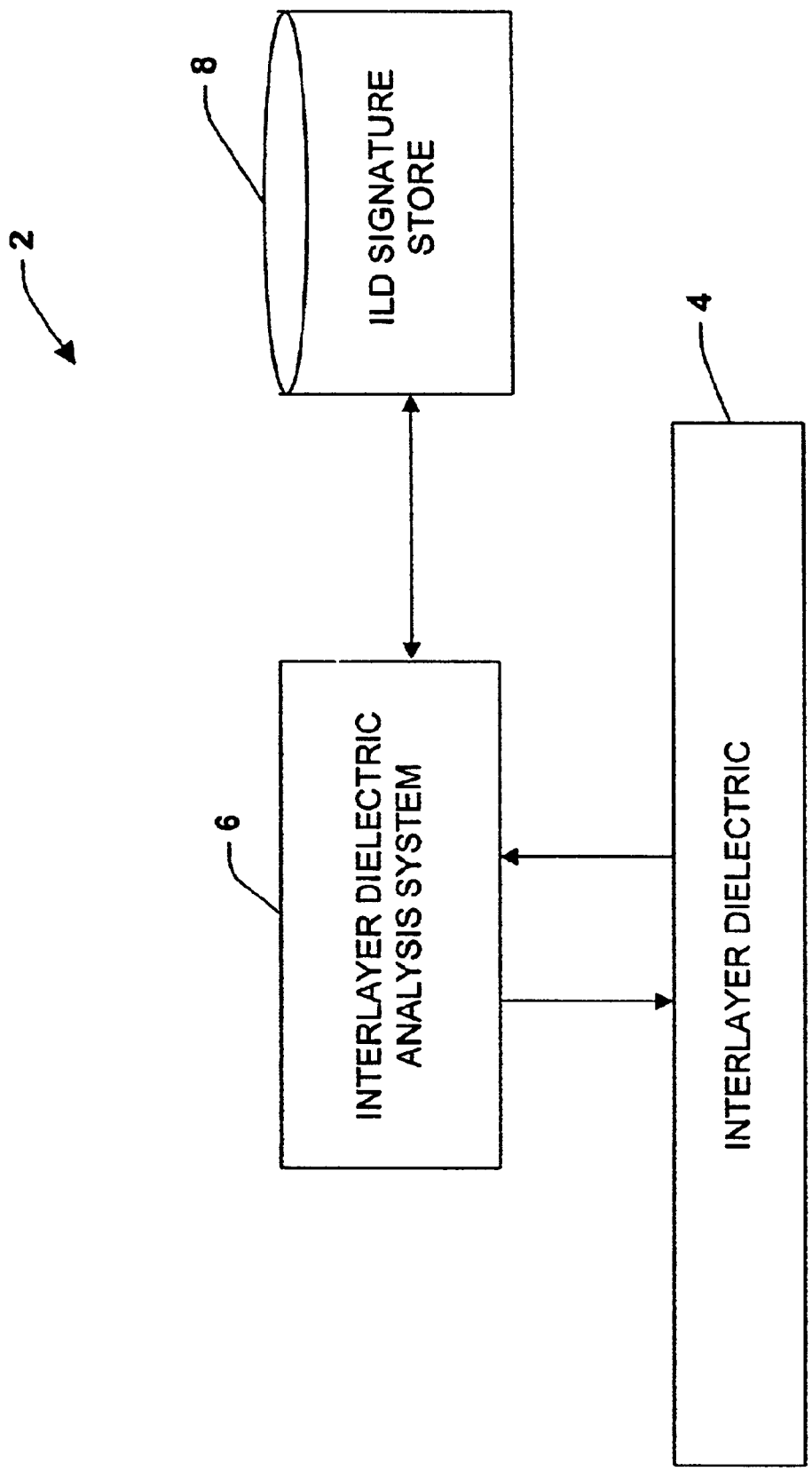
FIG. 1 is a schematic block diagram of an interlayer dielectric void detection system in accordance with the present invention.

The present invention will now be described with reference to the drawings, where like reference numerals are used to refer to like elements throughout. The present invention will be described with reference to a system and method for detecting and monitoring void formation in the inter layer dielectric (hereinafter "ILD"). The following detailed description reveals the best modes presently contemplated by the inventors for practicing the invention. It should be understood that the description of these preferred embodiments are merely illustrative and that they should not be taken in a limiting sense.

FIG. 1 illustrates an interlayer dielectric void detection system 2. The system 2 includes an interlayer dielectric analysis system 6 that analyzes an interlayer dielectric 4 for defects such as voids. The analysis system 6 employs a suitable tool (e.g., scatterometry system) to obtain a signature corresponding to the attributes of the ILD 4 being reviewed. The analysis system 6 obtains such signature and compares it to a database of historical ILD signatures stored in ILD signature store 8. The historical database of signatures provides for M number of profiles (M being an integer) relating to various ILD states. The analysis system 6 looks for similarity between the current signature and at least one of the historical signatures. Based on such comparison and other extrinsic data (e.g., process parameters) as well as other analytical tools, the analysis system 6 makes an inference as to the current state of the ILD 4 (e.g., if voids are present in the ILD).

It is to be appreciated that various aspects of the present invention may employ technologies associated with facilitating unconstrained optimization and/or minimization of error costs. Thus, non-linear training systems/methodologies (e.g., back propagation, Bayesian, fuzzy sets, non-linear regression, or other neural networking paradigms including mixture of experts, cerebella model arithmetic computer (CMACS), radial basis functions, directed search networks and function link networks) may be employed. Furthermore, as used in this application, the term "component" is intended to refer to a computer-related entity, either hardware, a combination of hardware and software, software, or software in execution. For example, a component may be, but is not limited to being, a process running on a processor, a processor, an object, an executable, a thread of execution, a program, and a computer. By way of illustration, both an application running on a server and the server can be a component.

Figure 2:
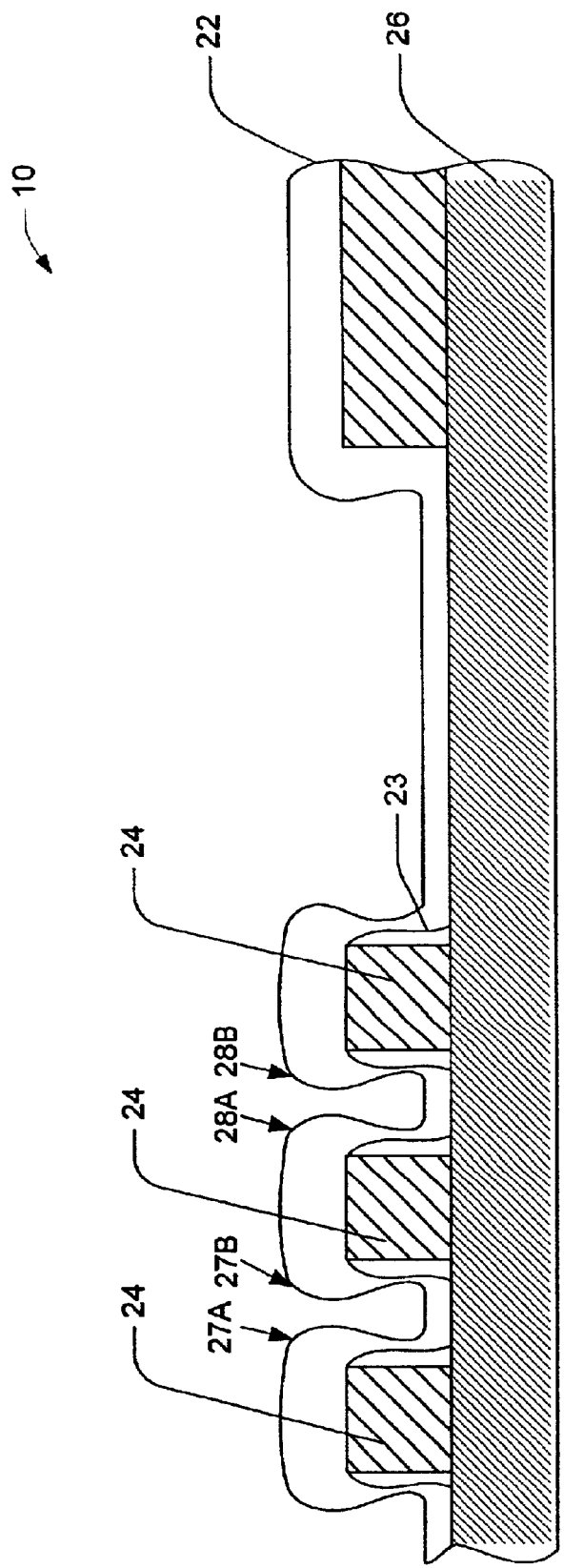
FIG. 2 illustrates a cross-sectional view of a semiconductor device in accordance with the present invention.
Figure 3:
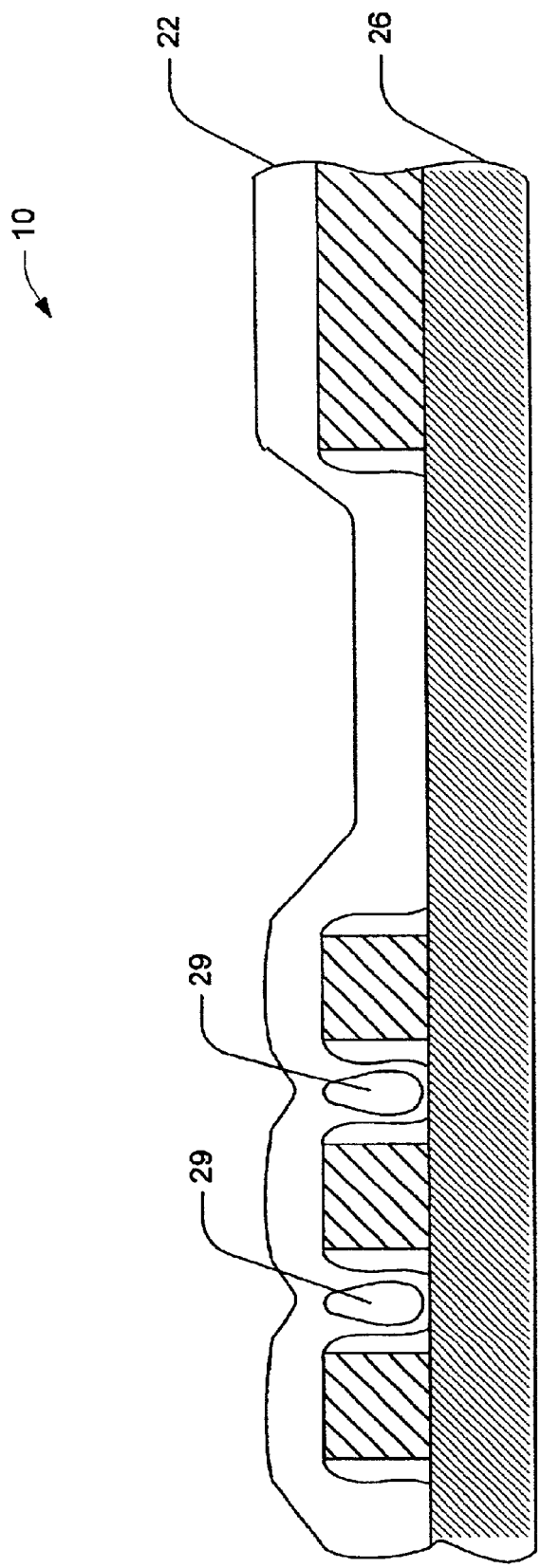
FIG. 3 illustrates a cross-sectional view of a semiconductor device having at least one void formed in accordance with the present invention.

Referring to FIGS. 2–3, a semiconductor device 10 undergoing fabrication processing is shown. In many conventional fabrication methods, the possibility of void formation in multi-layer devices is present, and generally, void formation continues undetected until fabrication is completed. Most voids are undesirable and lead to inoperable devices. FIGS. 2–3 illustrate one way void formation may occur during semiconductor fabrication. It should be appreciated that the present invention also encompasses other fabrication processes in which void formation may occur.

In FIG. 2, a semiconductor device 10 is shown. The semiconductor device 10 includes an ILD layer 22 deposited over semiconductor features 24 (e.g., gate, metal lines, etc.) having spacers 23 formed on either side of the features 24 as shown. The features 24 are formed on a semiconductor substrate 26. In FIG. 2, the potential for void formation is shown at corner positions 27A, 27B and 28A, 28B. Following ILD 22 deposition, the device 10 is subjected to a system for monitoring ILD deposition and detecting void formation, which will be discussed in more detail below. Using this system facilitates earlier detection of void formation, allowing a user to adjust fabrication parameters accordingly to mitigate further void formation.

FIG. 3 shows the device 10 after having undergone further processing such as sputter etching of the ILD layer 22. The sputter etch step associated with the ILD layer 22 has caused voids 29 to form. At this stage of processing, the device 10 may be subjected to a system 20 for monitoring ILD deposition and detecting void formation which will be described in greater detail.

Figure 4:
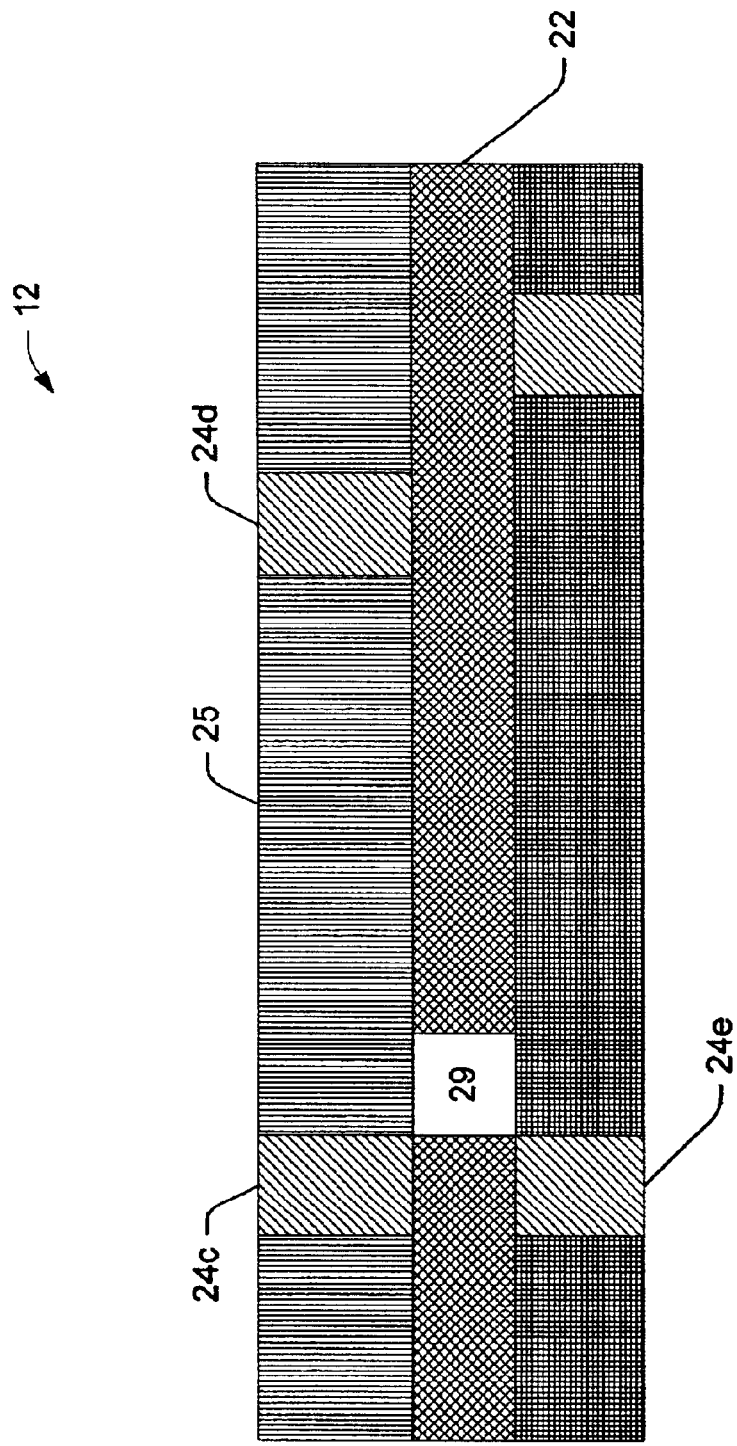
FIG. 4 is a schematic, cross-sectional view of a block diagram illustrating the presence of a void in accordance with the present invention.

FIG. 4 provides a cross-sectional view of a block diagram associated with a device 12 where void 29 has formed in the ILD layer 22. Features 24c and 24d are separated horizontally by a dielectric spacer 25. Similarly, the feature 24c and a feature 24e located in different layers are separated by an ILD layer 22 Because ILD layer 25 contains a void 29, problems may arise during the fabrication and/or in the operability of the completed device. For example, the void 29 may promote electrical interaction between the feature 24c and the feature 24e rather than electrical insulation between the layers. Depending on the purpose and application of the device, this undesired interaction may result in chip malfunction, circuit shorting, and/or decreased processing speed in the chip.

Figure 5:
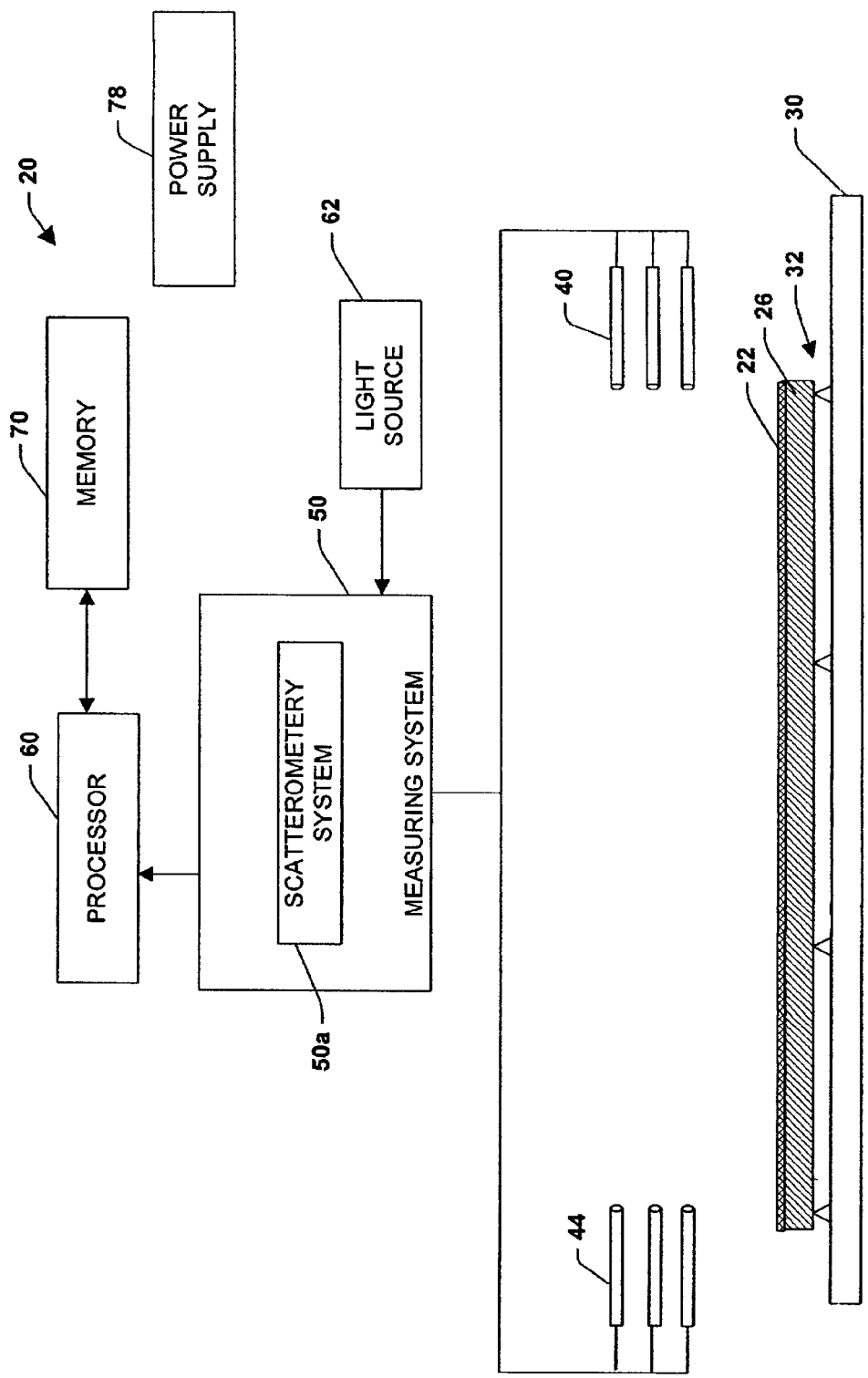
FIG. 5 is schematic block diagram of an ILD void monitoring system in accordance with the present invention.

Turning now to FIG. 5, the system 20 for monitoring deposition and processing of the ILD layer 22 is shown. The substrate 26, including the ILD layer 22 thereon, is supported over a chuck 30. The system 20 further includes one or more light detecting devices 40 (e.g., photo detectors, photo diodes) that are selectively controlled by the system 20 to facilitate detecting voids in the ILD layer 22. One or more light sources 44, which are selectively controlled by the system 20, project light onto respective portions of the ILD layer 22. Light reflected from the ILD layer 22 is processed by an ILD layer parameter measuring system 50 to measure at least one parameter relating to the presence of voids in the ILD layer 22. The reflected light may be processed with respect to the incident light in measuring the various parameters.

The measuring system 50 includes a scatterometry system 50a. It is to be appreciated that any suitable scatterometry system 50a may be employed to carry out the present invention and such systems are intended to fall within the scope of the claims appended hereto. Scatterometry systems are known in the art, and therefore further discussion related thereto is limited for sake of brevity.

A source of light 62 (e.g., a laser or polychromatic light) provides light to the one or more target light sources 44 via the measuring system 50. The light source 62 may be a frequency stabilized laser however it will be appreciated that any laser or other light source (e.g. laser diode or helium neon (HeNe) gas laser) suitable for carrying out the present invention may be employed.

A processor 60 receives the measured data from the measuring system 50 and determines whether voids are present in the respective portions of the ILD layer 22. The processor 60 is operatively coupled to the measuring system 50 and is programmed to control and operate the various components within the ILD void monitoring system 20 in order to carry out the various functions described herein. The processor (or a central processing unit) 60 may be any of a plurality of processors, such as the AMD Athlon, K7 and other similar and compatible processors. The manner in which the processor 60 may be programmed to carry out the functions relating to the present invention will be readily apparent based on the description provided herein. A memory 70 that is operatively coupled to the processor 60 is also included in the system 20 and serves to store program code executed by the processor 60 for carrying out operating functions of the system 20 as described herein. The memory 70 also serves as a storage medium for temporarily storing information such as ILD voids, ILD layer coordinate tables, scatterometry information, and other data that may be employed in carrying out the present invention.

A power supply 78 provides operating power to the system 20. Any suitable power supply (e.g., battery, line power) may be employed to carry out the present invention.

Figure 6:
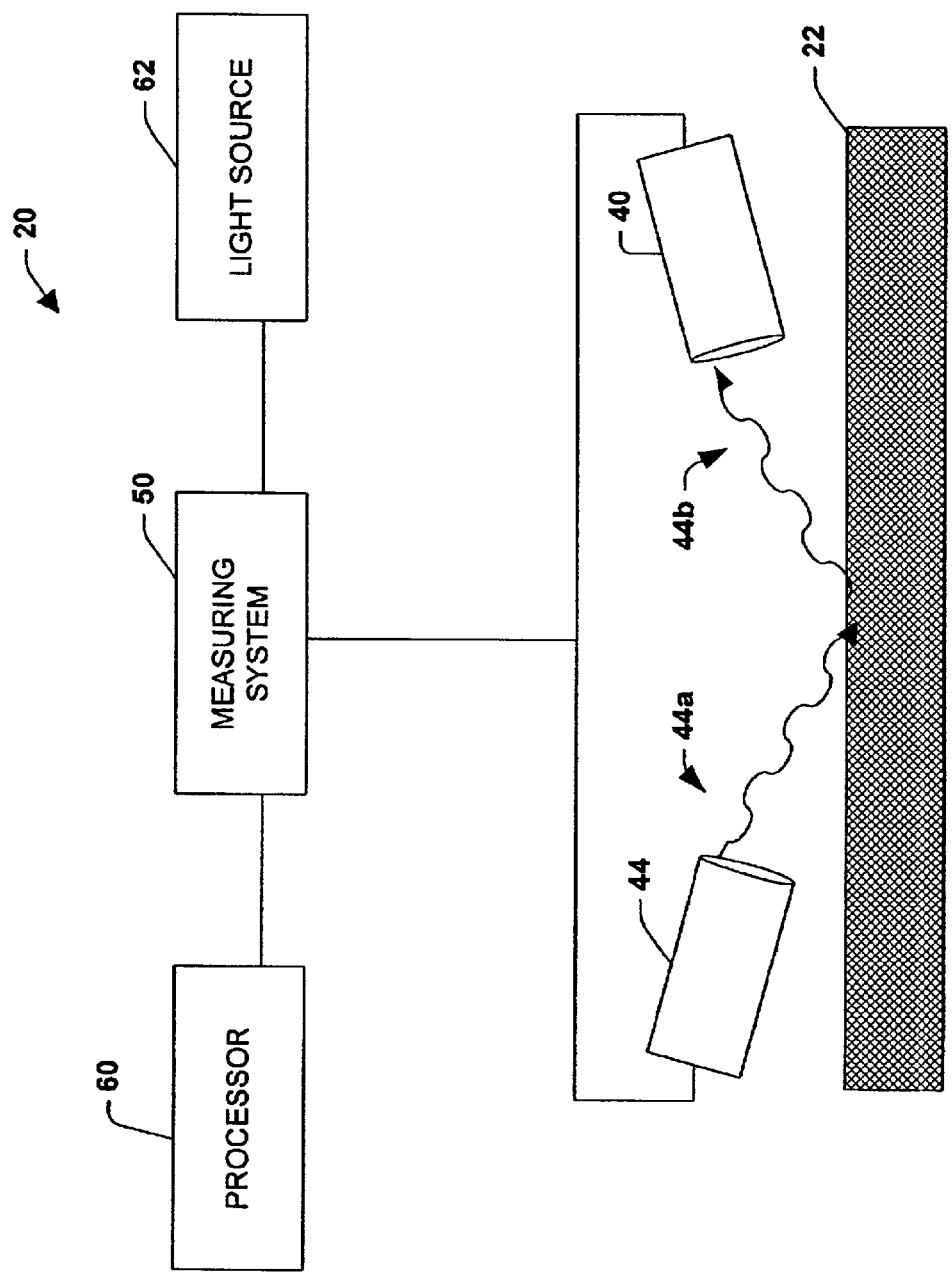
FIG. 6 is a partial schematic block diagram of the system of FIG. 5 being employed in connection with determining ILD voids by gathering reflected light in accordance with the present invention.

FIG. 6 illustrates the system 20 being employed to determine whether and to what extent void formation has occurred in a particular portion of the ILD layer 22. The target light source 44 directs a light 44a incident to the surface of the ILD layer 22. The reflected light 44b from the surface of the ILD may vary (e.g., variations in intensity and/or phase) in accordance with the presence or absence of voids in the ILD layer 22. A light detecting device 40 collects the reflected light 44b and passes the collected light to the measuring system 50, which processes the reflected light 44b in accordance with scatterometry techniques to provide the processor 60 with data corresponding to the presence or absence of voids in the ILD layer 22. The light detecting device 40 collects the reflected light 44b and passes data associated with the collected light to the measuring system 50, which processes such data in accordance with suitable techniques (e.g., scatterometry, spectroscopic ellipsometry) to provide the processor 60 with data corresponding to the presence or absence of voids in the ILD layer 22. The processor 60 analyzes the data and determines whether unacceptable voids appear in the ILD layer 22.

Alternatively, or in addition, the processor 60 employs a database (not shown) of known ILD layers having at least one void present and the reflected light date. associated with such layers. Incorporating a database allows the processor to communicate to what extent a void has formed (e.g., dimensions of the void) to a user by comparing the collected data with known voids. Obtaining this information facilitates determining whether the detected void is unacceptable to the user.

Figure 7:
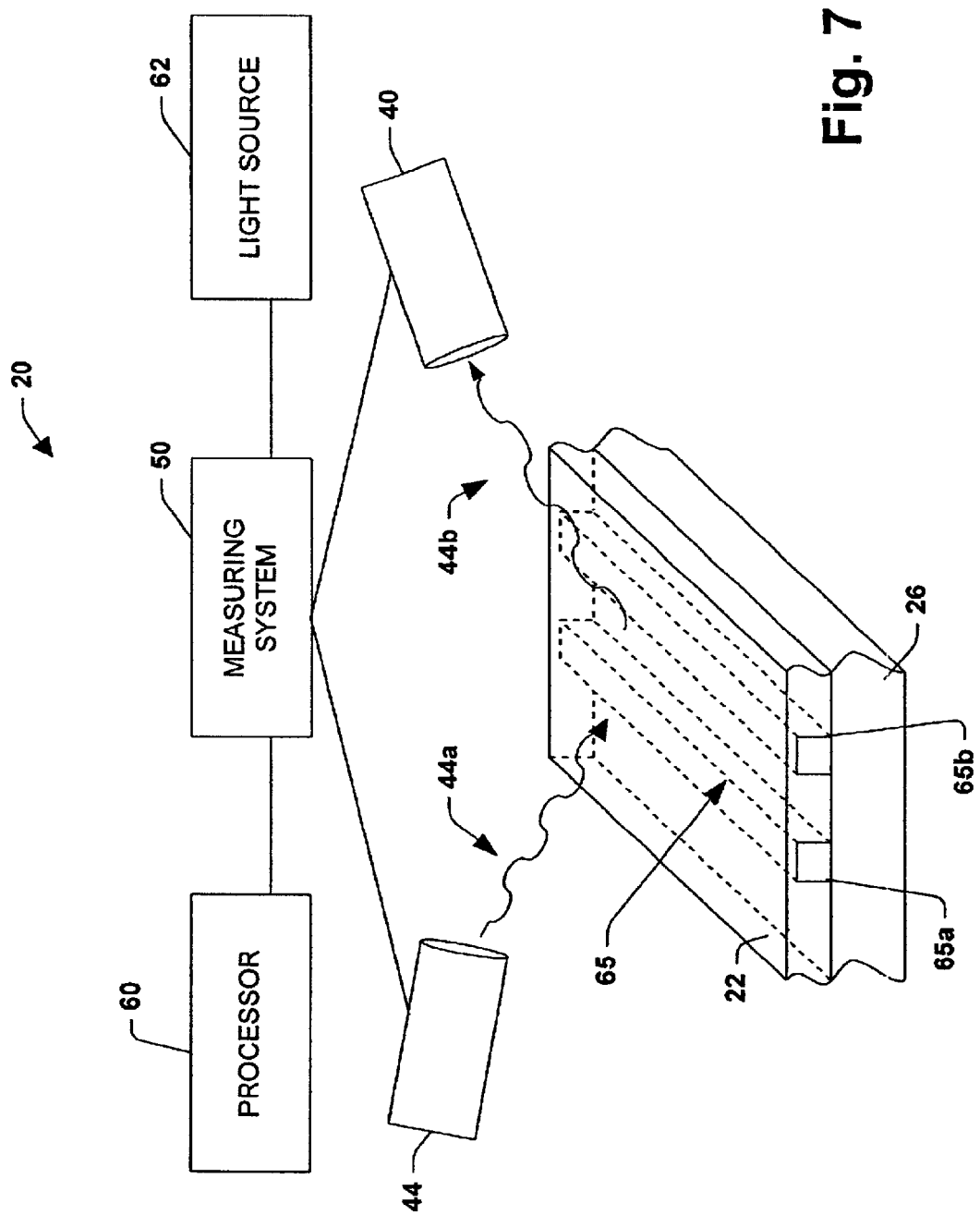
FIG. 7 is a partial schematic block diagram of the system of FIG. 5 being employed in connection with a grating formed on a wafer in accordance with the present invention.

FIG. 7 illustrates the system 20 being employed in connection with a grating 65 formed of a plurality of lines (e.g., lines 65a and 65b) to determine whether there are voids in the ILD layer 22 at a particular portion. The lines are adjacent to each other and although there are only two lines (e.g., lines 65a and 65b) illustrated for ease of understanding, it is to be appreciated than many thousands or even millions of such lines may be employed in the grating 65.

The target light source 44 directs the light 44a incident at the grating 65 in the ILD layer 22. The light detecting device 40 collects the reflected light 44b and passes data associated with the collected light to the measuring system 50, which processes such data in accordance with scatterometry techniques to provide the processor 60 with data corresponding to the presence or absence of voids in the ILD layer 22. The processor 60 analyzes the data and determines whether unacceptable voids appear in the ILD layer 22.

Turning now to FIG. 8, the chuck 30 is shown in perspective supporting the substrate 26 having an ILD layer 22 thereon. In FIG. 9, the ILD layer 22 may be divided into a grid pattern as is shown. Each grid block (XY) of the grid pattern corresponds to a particular portion of the ILD layer 22, and each portion is individually monitored for voids. Each respective portion of the ILD layer ($X_1Y_1 \ldots X_{12}, Y_{12}$) is monitored for voids using the one or more target light sources 44, the one or more light detecting devices 40, the measuring system 50 and the processor 60. The void measurements are a measure of how continuous the ILD layer 22 is over an area. The void measurement of the ILD layer 22 at coordinate $X_7Y_6$ is substantially higher than the void measurement of the other ILD layer 22 portions XY. It is to be appreciated that although FIG. 9 illustrates the ILD layer 22 being mapped (partitioned) into 144 grid block portions, the ILD layer 22 may be mapped with any suitable number of portions. Although the present invention is described with respect to one target light source 44 corresponding to one grid block XY, it is to be appreciated that any suitable number of target light sources 44 may correspond to any suitable number of grid blocks XY.

FIG. 10 is a representative table of void measurements taken at the various grid blocks that have been correlated with acceptable void measurement values for the portions of the ILD layer 22 mapped by the respective grid blocks. As can be seen, all the grid blocks except grid block $X_7Y_6$ have void measurements corresponding to an acceptable void table value ($T_A$) (e.g., are within an expected range of void measurements), while grid block $X_7Y_6$ has an undesired void table value ($T_U$). Thus, the processor 60 has determined that an undesirable void condition exists at the portion of the ILD layer 22 mapped by grid block $X_7Y_6$. Accordingly, the processor 60 can mark the portion of the ILD layer 22 mapped at grid block $X_7Y_6$ to allow, for further processing and/or to permit destruction of the ILD layer 22 and/or device.

Figure 11:
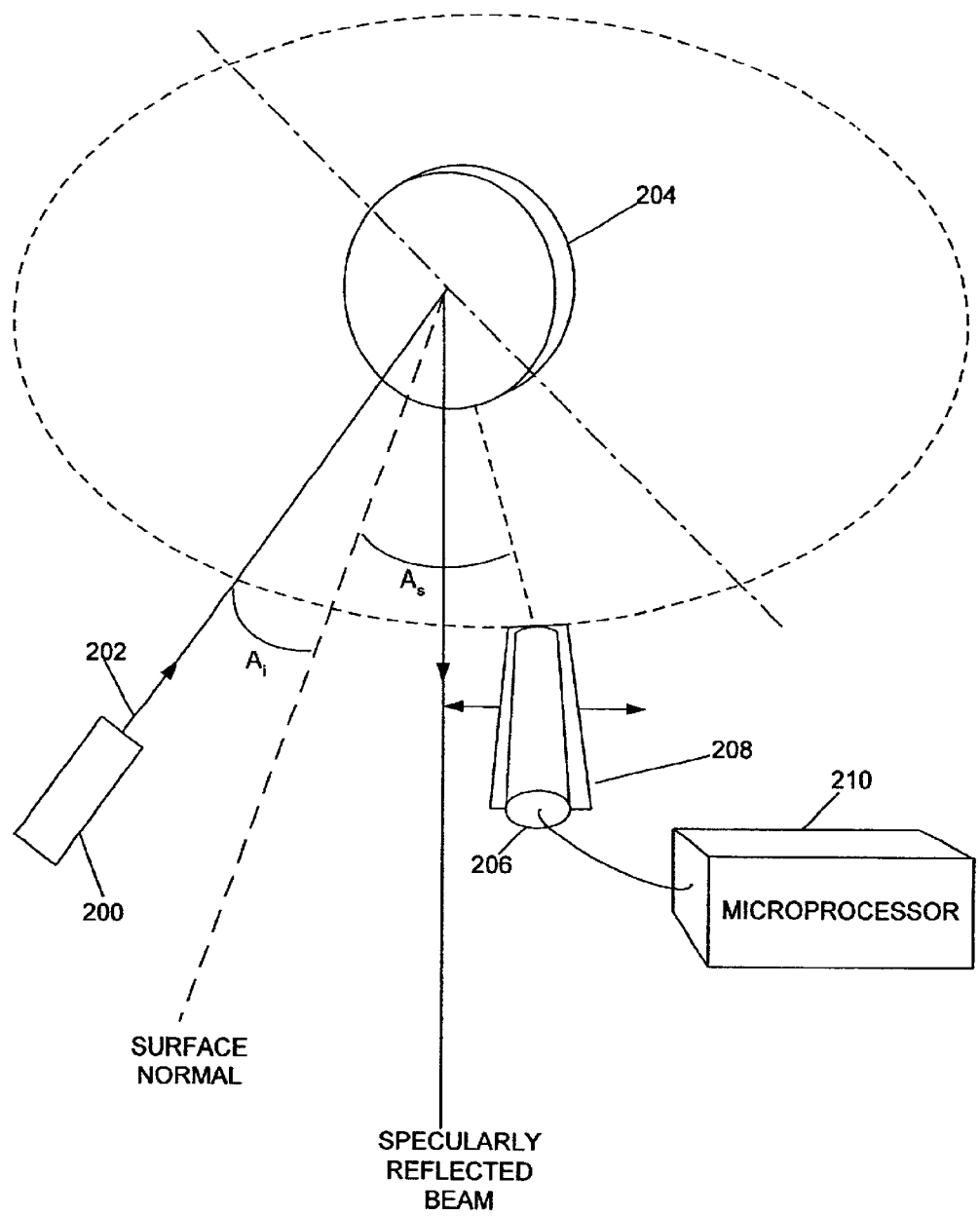
FIG. 11 illustrates an exemplary scatterometry system collecting reflected light.

FIG. 11 illustrates an exemplary scatterometry system collecting reflected light. Light from a laser 200 is brought to focus in any suitable well-known manner to form a beam 202. A sample, such as a wafer 204 is placed in the path of the beam 202 and a photo detector or photo multiplier 206 of any suitable well-known construction. Different detector methods may be employed to determine the scattered power. To obtain a grating pitch, the photo detector or photo multiplier 206 may be mounted on a rotation stage 208 of any suitable well-known design. A microprocessor 210 of any suitable well-known design may be used to process detector readouts, including but not limited to angular locations of different diffracted orders leading to diffraction grating pitches being calculated. Thus, light reflected from the sample 204 may be accurately measured.

Figure 12:
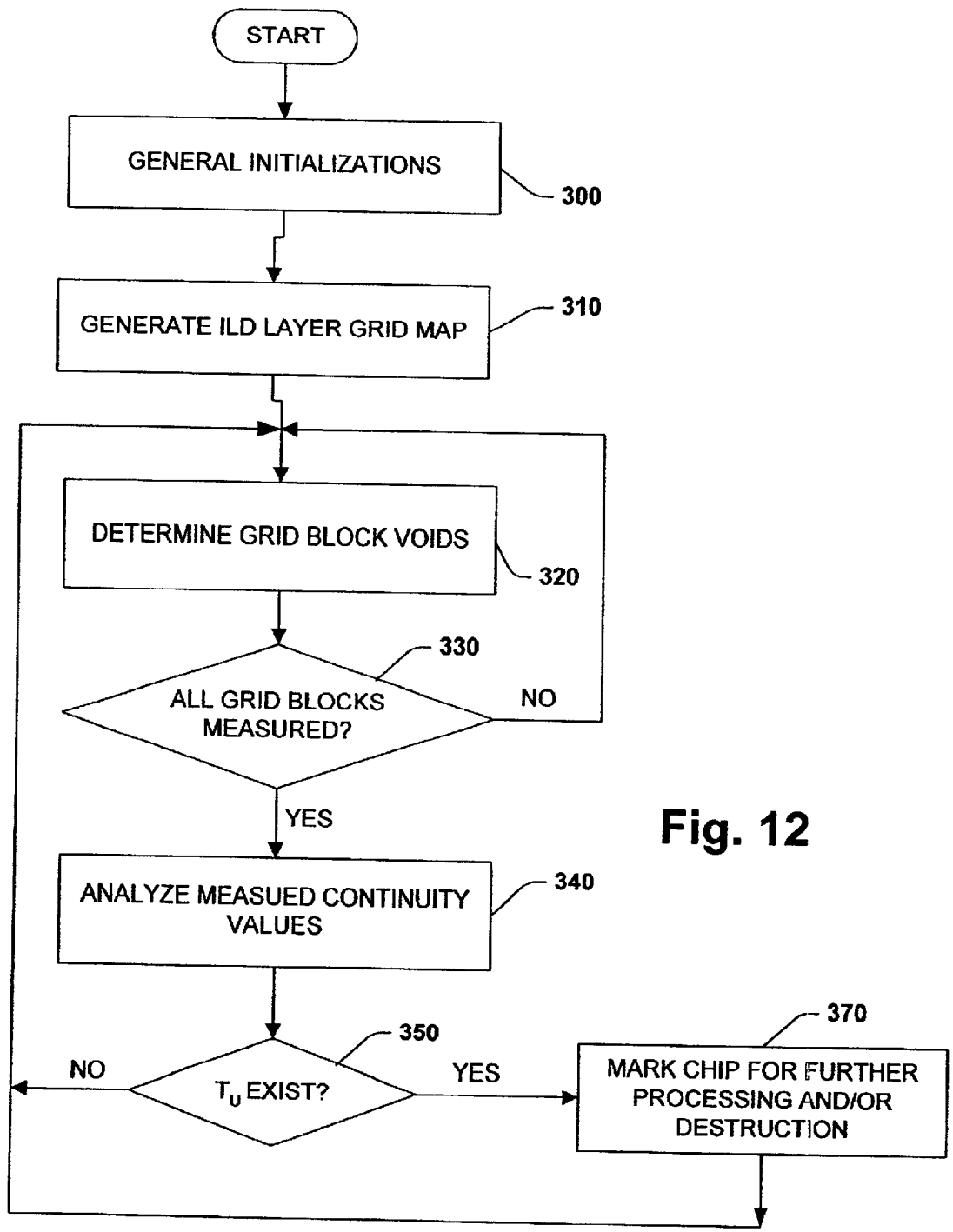
FIG. 12 is a flow diagram illustrating one specific methodology for carrying out the present invention.

In view of the exemplary systems shown and described above, methodologies that may be implemented in accordance with the present invention will be better appreciated with reference to the flow chart of FIG. 12. While, for purposes of simplicity of explanation, the methodologies are shown and described as a series of blocks, it is to be understood and appreciated that the present invention is not limited by the order of the blocks, as some blocks can, in accordance with the present invention, occur in different orders and/or concurrently with other blocks from that shown and described herein. Moreover, not all illustrated blocks may be required to implement a methodology in accordance with the present invention.

FIG. 12 is a flow diagram illustrating one particular methodology for carrying out the present invention. At 300, the processor 60 performs general initializations to the ILD void detecting system 20. At 310, the processor 60 maps at least a portion of the ILD layer 22 into a plurality of grid blocks "XY". At 320, void determinations are made with respect to the various WLD portions mapped by the respective grid blocks XY. At 330, the processor 60 determines if all grid block measurements have been taken. If no, the processor 60 returns to step 320. If yes, the processor 60 analyzes the determined void values against a table of acceptable void values for the respective portions of the ILD layer 22 (block 340). At 350, the processor 60 determines if any void values are unacceptable. If all void values are acceptable, the processor 60 returns to 320 to perform another iteration. If unacceptable void values are found for any of the grid blocks, the processor 60 advances to 370 where the unacceptable void values are analyzed. After the analyses, the processor 60 may mark the grid block and/or chip for further processing and/or destruction. The process then returns to 320 to perform another iteration. It is to be appreciated by one skilled in the art that although an iterative multi-step process is described above, a single step, set of parallel-processing steps or multi-step processes may be employed in the present invention.

Scatterometry is a technique for extracting information about a surface upon which an incident light has been directed. Information concerning properties including, but not limited to, dishing, erosion, profile, thickness of thin films and critical dimensions of features present on the surface can be extracted. The information can be extracted by comparing the phase and/or intensity of the light directed onto the surface with phase and/or intensity signals of a complex reflected and/or diffracted light resulting from the incident light reflecting from and/or diffracting through the surface upon which the incident light was directed. The intensity and/or the phase of the reflected and/or diffracted light will change based on properties of the surface upon which the light is directed. Such properties include, but are not limited to, the chemical properties of the surface, the planarity of the surface, features on the surface, voids in the surface, and the number and/or type of layers beneath the surface.

Different combinations of the above-mentioned properties will have different effects on the phase and/or intensity of the incident light resulting in substantially unique intensity/phase signatures in the complex reflected and/or diffracted light. Thus, by examining a signal (signature) library of intensity/phase signatures, a determination can be made concerning the properties of the surface. Such substantially unique phase/intensity signatures are produced by light reflected from and/or refracted by different surfaces due, at least in part, to the complex index of refraction of the surface onto which the light is directed. The complex index of refraction (N) can be computed by examining the index of refraction (n) of the surface and an extinction coefficient (k). One such computation of the complex index of refraction can be described by the equation:

$$N=n-jk$$

where j is an imaginary number.

The signal (signature) library can be constructed from observed intensity/phase signatures and/or signatures generated by modeling and simulation. By way of illustration, when exposed to a first incident light of known intensity, wavelength and phase, a first feature on a wafer can generate a first phase/intensity signature. Similarly, when exposed to the first incident light of known intensity, wavelength and phase, a second feature on a wafer can generate a second phase/intensity signature. For example, a line of a first width may generate a first signature while a line of a second width may generate a second signature. Observed signatures can be combined with simulated and modeled signatures to form the signal (signature) library. Simulation and modeling can be employed to produce signatures against which measured phase/intensity signatures can be matched. In one exemplary aspect of the present invention, simulation, modeling and observed signatures are stored in a signal (signature) library containing over three hundred thousand phase/intensity signatures. Thus, when the phase/intensity signals are received from scatterometry detecting components, the phase/intensity signals can be pattern matched, for example, to the library of signals to determine whether the signals correspond to a stored signature.

Figure 13:
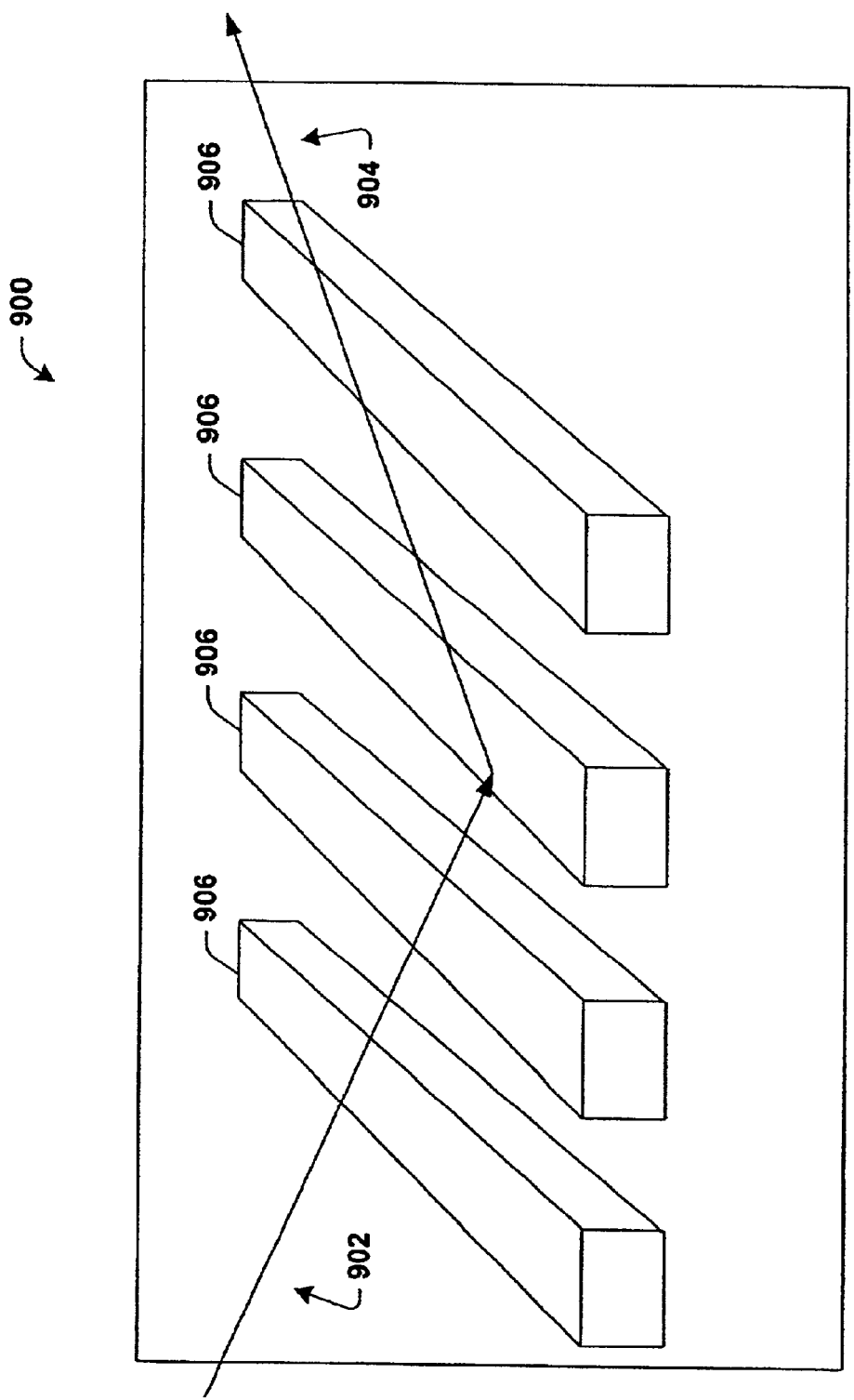
FIG. 13 is a simplified perspective view of an incident light reflecting off a surface, in accordance with an aspect of the present invention.
Figure 18:
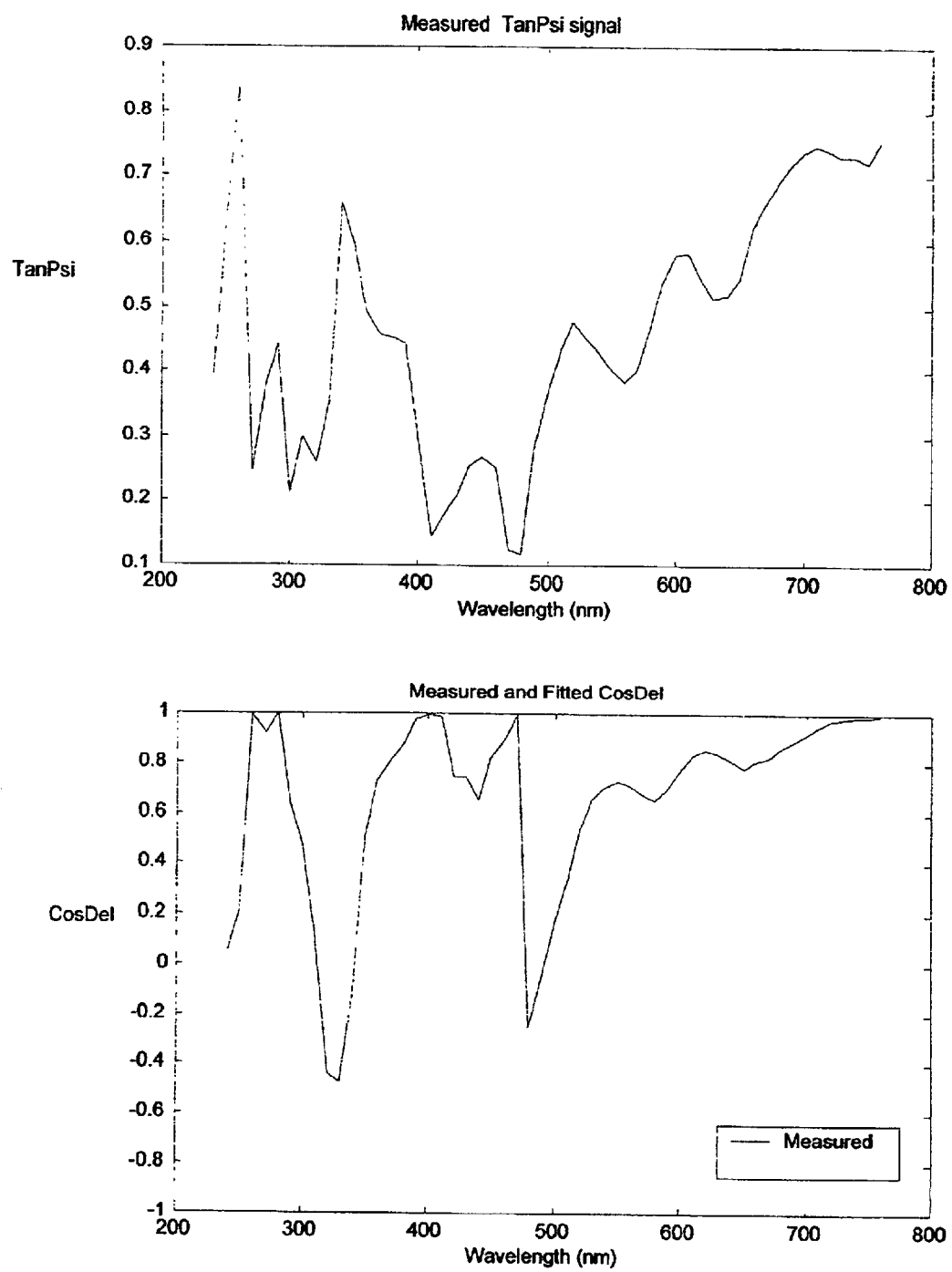
FIG. 18 illustrates phase and intensity signals recorded from a complex reflected and refracted light produced when an incident light is directed onto a surface, in accordance with an aspect of the present invention.

To illustrate the principles described above, reference is now made to FIGS. 13 through 18. Referring initially to FIG. 13, an incident light 902 is directed at a surface 900, upon which one or more features 906 may exist. In FIG. 13 the incident light 902 is reflected as reflected light 904. The properties of the surface 900, including but not limited to, thickness, uniformity, planarity, chemical composition and the presence of features, can affect the reflected light 904. In FIG. 13, the features 906 are raised upon the surface 900. The phase and intensity of the reflected light 904 can be measured and plotted, as shown, for example, in FIG. 18. The phase 960 of the reflected light 904 can be plotted, as can the intensity 962 of the reflected light 904. Such plots can be employed to compare measured signals with signatures stored in a signature library using techniques like pattern matching, for example.

Figure 14:
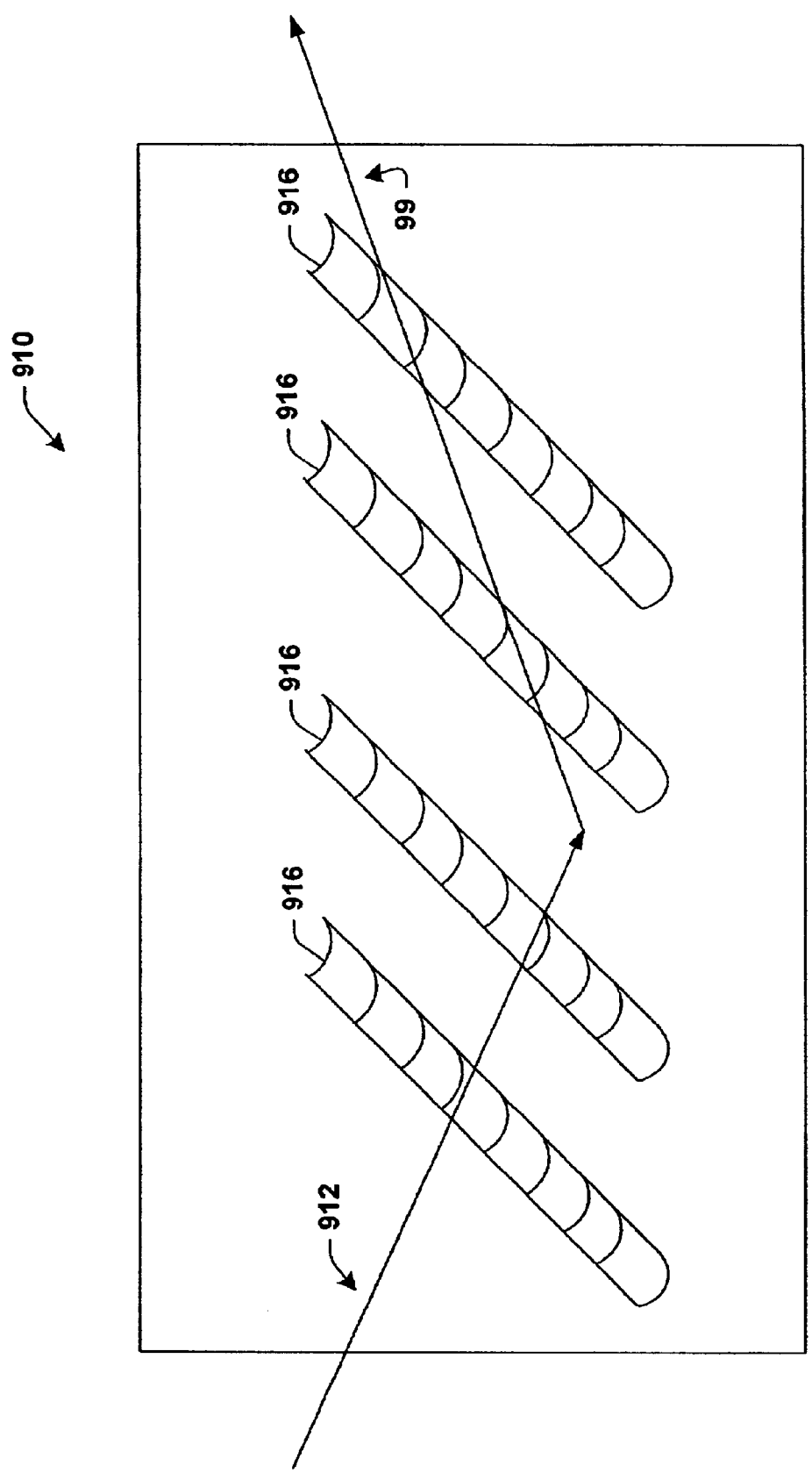
FIG. 14 is a simplified perspective view of an incident light reflecting off a surface, in accordance with an aspect of the present invention.

Referring now to FIG. 14, an incident light 912 is directed onto a surface 910 upon which one or more depressions 916 appear. The incident light 912 is reflected as reflected light 914. Like the one or more features 906 (FIG. 13) may affect an incident beam, so too may the one or more depressions 916 affect an incident beam. Thus, it is to be appreciated by one skilled in the art that scatterometry can be employed to measure features appearing on a surface, features appearing in a surface, and properties of a surface itself, regardless of features.

Figure 15:
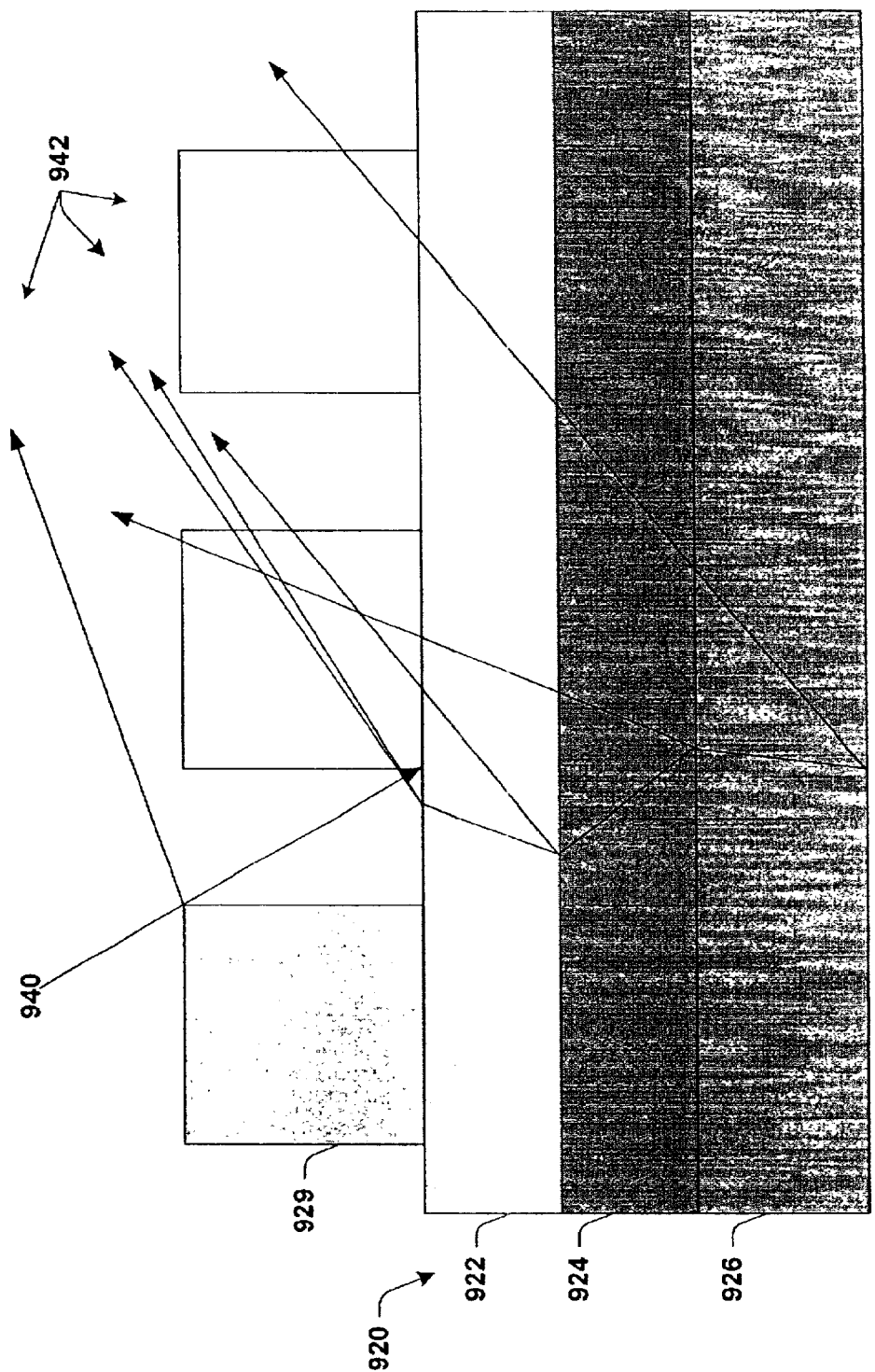
FIG. 15 illustrates a complex reflected and refracted light produced when an incident light is directed onto a surface, in accordance with an aspect of the present invention.

Turning now to FIG. 15, complex reflections and refractions of an incident light 940 are illustrated. The reflection and refraction of the incident light 940 can be affected by factors including, but not limited to, the presence of one or more features 928, and the composition of the substrate 920 upon which the features 928 reside. For example, properties of the substrate 920 including, but not limited to the thickness of a layer 922, the chemical properties of the layer 922, the opacity and/or reflectivity of the layer 922, the thickness of a layer 924, the chemical properties of the layer 924, the opacity and/or reflectivity of the layer 924, the thickness of a layer 926, the chemical properties of the layer 926, and the opacity and/or reflectivity of the layer 926 can affect the reflection and/or refraction of the incident light 940. Thus, a complex reflected and/or refracted light 942 may result from the incident light 940 interacting with the features 928, and/or the layers 922, 924 and 926. Although three layers 922, 924 and 926 are illustrated in FIG. 15, it is to be appreciated by one skilled in the art that a substrate can be formed of a greater or lesser number of such layers.

Figure 16:
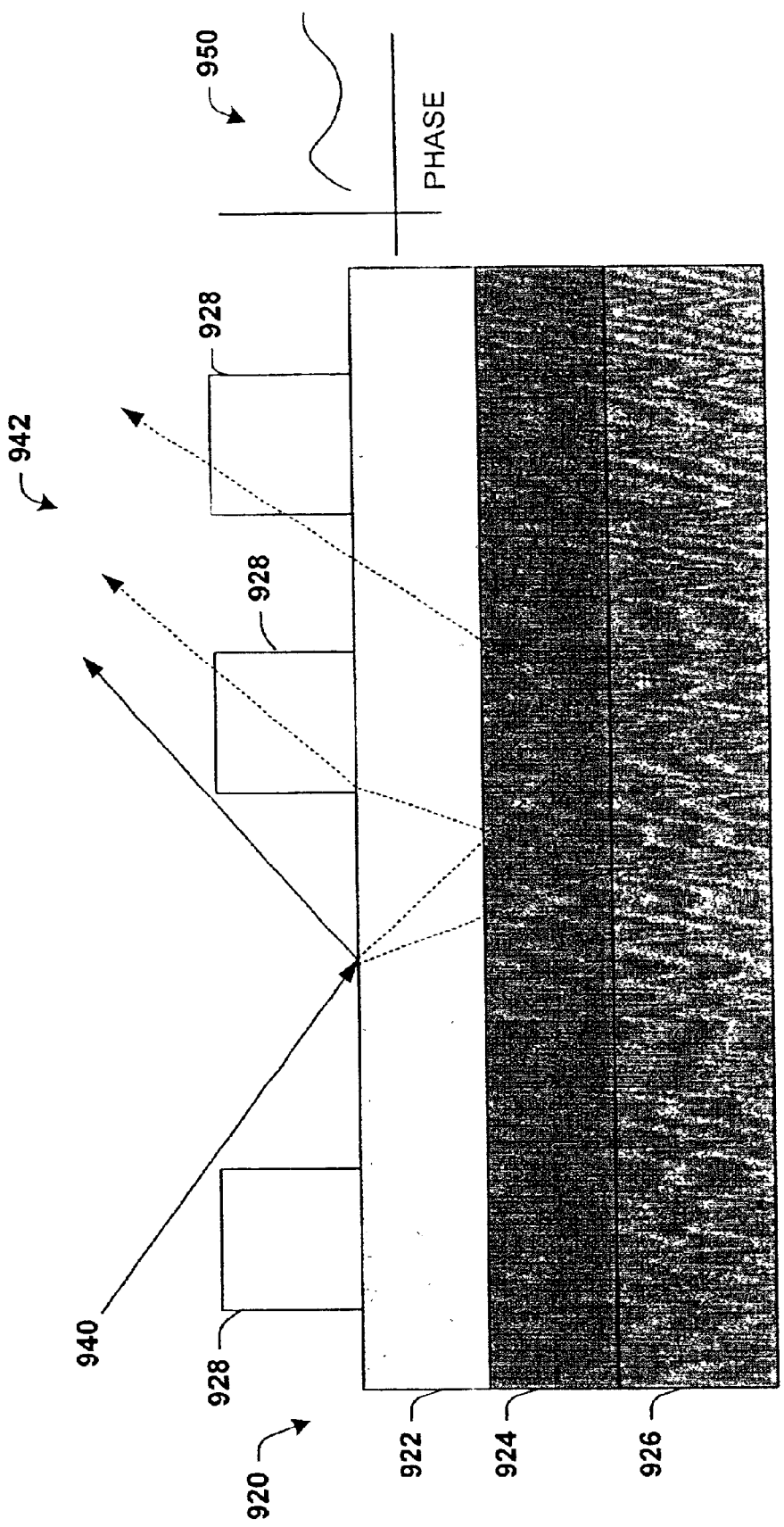
FIG. 16 illustrates a complex reflected and refracted light produced when an incident light is directed onto a surface, in accordance with an aspect of the present invention.
Figure 17:
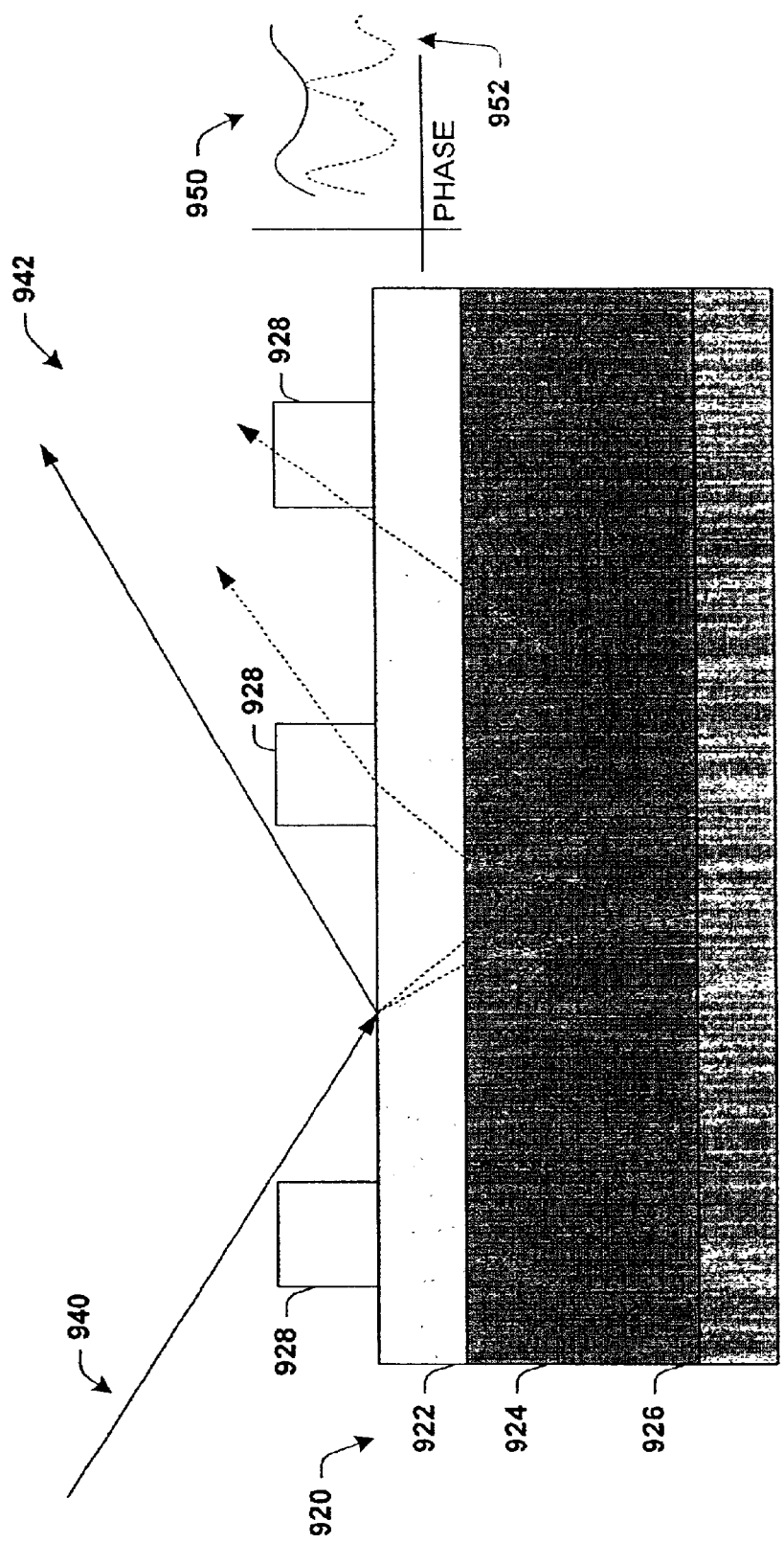
FIG. 17 illustrates a complex reflected and refracted light produced when an incident light is directed onto a surface, in accordance with an aspect of the present invention.

Turning now to FIG. 16, one of the properties from FIG. 15 is illustrated in greater detail. The substrate 920 can be formed of one or more layers 922, 924 and 926. The phase 950 of the reflected and/or refracted light 942 can depend, at least in part, on the thickness of a layer, for example, the layer 924. Thus, in FIG. 17, the phase 952 of the reflected light 942 differs from the phase 950 due, at least in part, to the different thickness of the layer 924 in FIG. 17.

Thus, scatterometry is a technique that can be employed to extract information about a surface upon which an incident light has been directed. The information can be extracted by analyzing phase and/or intensity signals of a complex reflected and/or diffracted light. The intensity and/or the phase of the reflected and/or diffracted light will change based on properties of the surface upon which the light is directed, resulting in substantially unique signatures that can be analyzed to determine one or more properties of the surface upon which the incident light was directed.

The present invention provides for a system and method for detecting ILD voids. As a result, the present invention facilitates improving semiconductor integrity and reliability, which in turn affords increases in quality in accordance with the present invention.

Described above are preferred aspects of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

What is claimed is:

1. A system for detecting and monitoring ILD void formation, comprising:
   a light source directed to at least one portion of an ILD layer;
   a measuring system for measuring parameters of the ILD layer based on light reflected from the at least one portion of the ILD layer; and
   a processor operatively coupled to the measuring system, the processor receiving ILD layer parameter data from the measuring system and the processor using the data to determine the presence of a void in the ILD layer.

2. The system of claim 1, the measuring system further including a scattrometry system for processing the light reflected from the ILD layer.

3. The system of claim 1, where the measuring system further measures parameters of the ILD layer based on light passing through the ILD layer.

4. The system of claim 3, the processor being operatively coupled to the scatterometry system, the processor analyzing data relating to ILD voids received from the scatterometry system, and the processor basing a determination of whether an ILD void exists at least partially on the analyzed data.

5. The system of claim 4, the data further relating to thickness of the ILD layer.

6. The system of claim 1, the processor mapping the ILD layer into a plurality of grid blocks, detecting the presence of an ILD void at a grid block, and comparing it to known ILD void values to determine the dimensions of the void.

7. The system of claim 6, where the processor determines the existence of an unacceptable ILD void for at least a portion of the ILD layer based upon the determined ILD void differing from an acceptable value.

8. A method for detecting and monitoring ILD void formation, comprising:
   defining an ILD layer as a plurality of portions;
   directing light onto at least one of the portions;
   collecting light reflected from the at least one portion;
   comparing a reflected light array from the at least one portion to a database, where the database comprises known ILD layers having at least one void present, to determine the presence of the at least one void in the at least one portion associated with the ILD layer; and
   selectively marking an ILD layer portion as having the at least one void.

9. The method of claim 8, further comprising using a scatterometry system to process the reflected light.

10. A method for detecting and monitoring ILD void formation, comprising:
    partitioning an ILD layer into a plurality of grid blocks;
    directing light onto at least one of the grid blocks;
    collecting light reflected from the at least one grid block;
    comparing a reflected light array from the at least one grid block to a database, where the database comprises known ILD layers having at least one void present, to determine the presence of the at least one void in the at least one portion associated with the ILD layer, and
    selectly marking the ILD layer grid block as having the at least one void, where the ILD layer grid block corresponds to a portion of the ILD layer.

11. A system for detecting ILD void formation, comprising:
    means for detecting ILD void formation in a plurality of portions of the ILD layer and;
    means for selectively marking an ILD layer portion as having a void formed therein.

* * * * *